(12) United States Patent
Chav et al.

(10) Patent No.: US 12,376,919 B2
(45) Date of Patent: Aug. 5, 2025

(54) ROBOTIC DEVICE AND STERILIZATION UNIT FOR SURGICAL INSTRUMENT

(71) Applicant: Orthosoft ULC, Montreal (CA)

(72) Inventors: Ramnada Chav, Laval (CA); Pierre Couture, Montreal (CA)

(73) Assignee: Orthosoft ULC, Montreal (CA)

( * ) Notice: Subject to any disclaimer, the term of this patent is extended or adjusted under 35 U.S.C. 154(b) by 1056 days.

(21) Appl. No.: 17/376,696

(22) Filed: Jul. 15, 2021

(65) Prior Publication Data

US 2022/0015841 A1 Jan. 20, 2022

Related U.S. Application Data

(60) Provisional application No. 63/052,137, filed on Jul. 15, 2020.

(51) Int. Cl.
| | |
|---|---|
| *A61L 2/00* | (2006.01) |
| *A61B 34/00* | (2016.01) |
| *A61B 34/30* | (2016.01) |
| *A61B 50/30* | (2016.01) |
| *A61B 90/00* | (2016.01) |
| *A61L 2/07* | (2006.01) |

(Continued)

(52) U.S. Cl.
CPC ............. *A61B 34/30* (2016.02); *A61B 34/25* (2016.02); *A61B 50/30* (2016.02); *A61B 90/36* (2016.02); *A61L 2/07* (2013.01); *A61L 2/10* (2013.01); *A61L 2/18* (2013.01); *A61L 2/24* (2013.01); *G06F 3/017* (2013.01); *G06F 3/041* (2013.01); *G06F 3/167* (2013.01); *G06T 7/20* (2013.01); *G06T 7/30* (2017.01); *G06T 7/70* (2017.01); *G06T 19/006* (2013.01); *A61B* *2090/365* (2016.02); *A61L 2202/122* (2013.01); *A61L 2202/14* (2013.01); *A61L 2202/16* (2013.01); *A61L 2202/18* (2013.01); *A61L 2202/24* (2013.01); *G06T 2200/04* (2013.01); *G06T 2200/24* (2013.01)

(58) Field of Classification Search
CPC ....... A61B 17/16; A61B 1/00006; A61B 1/05; A61B 34/30; A61B 90/37; A61L 2/00; A61L 24/00
USPC ................................ 422/26, 28, 292; 604/30
See application file for complete search history.

(56) References Cited

U.S. PATENT DOCUMENTS

| | | |
|---|---|---|
| 9,855,152 B2 | 1/2018 | Murphy |
| 10,016,287 B2 | 7/2018 | Murphy et al. |

(Continued)

OTHER PUBLICATIONS

"U.S. Appl. No. 17/376,676, Final Office Action mailed Apr. 7, 2023", 16 pgs.

(Continued)

*Primary Examiner* — Monzer R Chorbaji
(74) *Attorney, Agent, or Firm* — SCHWEGMAN LUNDBERG & WOESSNER, P.A.

(57) ABSTRACT

A method or system for storing an instrument, such as in a sterile environment. For example, a surgical robotic system may include a surgical robotic arm and a sterilization unit enclosing the sterile environment and storing the instrument. A processor may be used to determine that the instrument is needed (e.g., during a surgical procedure or portion of a surgical procedure or for a future surgical procedure or portion of a future surgical procedure). The processor may provide access to the instrument.

14 Claims, 10 Drawing Sheets

(51) Int. Cl.
*A61L 2/10* (2006.01)
*A61L 2/18* (2006.01)
*A61L 2/24* (2006.01)
*A61M 1/00* (2006.01)
*G06F 3/01* (2006.01)
*G06F 3/041* (2006.01)
*G06F 3/16* (2006.01)
*G06T 7/20* (2017.01)
*G06T 7/30* (2017.01)
*G06T 7/70* (2017.01)
*G06T 19/00* (2011.01)

(56) References Cited

U.S. PATENT DOCUMENTS

| | | | |
|---|---|---|---|
| 10,621,436 | B2 | 4/2020 | Wells et al. |
| 11,045,329 | B1 | 6/2021 | Murphy |
| 11,490,832 | B2 | 11/2022 | Murphy |
| 11,638,613 | B2 | 5/2023 | Murphy |
| 2007/0249967 | A1 | 10/2007 | Buly et al. |
| 2009/0088634 | A1 | 4/2009 | Zhao et al. |
| 2010/0010506 | A1 | 1/2010 | Murphy |
| 2014/0058407 | A1 | 2/2014 | Tsekos et al. |
| 2014/0275760 | A1 | 9/2014 | Lee et al. |
| 2015/0005785 | A1 | 1/2015 | Olson |
| 2015/0265368 | A1 | 9/2015 | Chopra et al. |
| 2015/0366628 | A1 | 12/2015 | Ingmanson |
| 2016/0239963 | A1 | 8/2016 | Kariv et al. |
| 2016/0331474 | A1 | 11/2016 | Lacal et al. |
| 2016/0354155 | A1 | 12/2016 | Hodges et al. |
| 2017/0258526 | A1 | 9/2017 | Lang |
| 2018/0049832 | A1* | 2/2018 | Eckert .................... A61B 34/30 |
| 2018/0082480 | A1 | 3/2018 | White et al. |
| 2018/0256258 | A1 | 9/2018 | Nash et al. |
| 2020/0337789 | A1 | 10/2020 | Meglan |
| 2020/0367990 | A1 | 11/2020 | Hale |
| 2021/0282887 | A1 | 9/2021 | Wiggermann |
| 2021/0290310 | A1 | 9/2021 | Laby et al. |
| 2022/0000562 | A1 | 1/2022 | Murphy et al. |
| 2022/0020219 | A1 | 1/2022 | Chav et al. |

OTHER PUBLICATIONS

"U.S. Appl. No. 17/376,676, Response filed Dec. 19, 2022 to Non Final Office Action mailed Sep. 19, 2022", 10 pgs.

"U.S. Appl. No. 17/376,676, Non Final Office Action mailed Sep. 19, 2022", 14 pgs.

U.S. Appl. No. 17/376,676, filed Jul. 15, 2021, Augmented Reality Bone Landmark Display.

"U.S. Appl. No. 17/376,676, Response filed Jun. 7, 2023 to Final Office Action mailed Apr. 7, 2023", 10 pgs.

"U.S. Appl. No. 17/376,676, Advisory Action mailed Jun. 15, 2023", 3 pgs.

"U.S. Appl. No. 17/376,676, Non Final Office Action mailed Aug. 11, 2023", 19 pgs.

"U.S. Appl. No. 17/376,676, Pre-Appeal Brief Request for Review filed Nov. 13, 2023", 4 pgs.

"U.S. Appl. No. 17/376,676, Pre-Appeal Brief Request filed Nov. 13, 2023", 4 pgs.

"U.S. Appl. No. 17/376,676, Decision on Pre-Appeal Brief Request mailed Nov. 27, 2023", 2 pgs.

"U.S. Appl. No. 17/376,676, Appeal Brief filed Jan. 16, 2024", 17 pgs.

"U.S. Appl. No. 17/376,676, Examiner's Answer mailed May 6, 2024", 17 pgs.

"U.S. Appl. No. 17/376,676, Reply Brief filed Jul. 8, 2024", 5 pgs.

* cited by examiner

ROBOTIC DEVICE AND STERILIZATION UNIT FOR SURGICAL INSTRUMENT

CLAIM OF PRIORITY

This application claims the benefit of priority to U.S. Provisional Application No. 63/052,137 filed Jul. 15, 2020, titled "INSTRUMENT PREPARATION AND VALIDATION," which is hereby incorporated herein by reference in its entirety.

BACKGROUND

Surgical advancements have allowed surgeons to use preoperative planning, display devices within a surgical field, optical imaging, and guides to improve surgical outcomes and customize surgery for a patient. While these advances have allowed for quicker and more successful surgeries, they ultimately rely on physical objects, which have costs and time requirements for manufacturing and configuration. Physical objects and devices may also obstruct portions of a surgical field, detracting from their benefits.

Computer-assisted surgery is a growing field that encompasses a wide range of devices, uses, procedures, and computing techniques, such as surgical navigation, preoperative planning, and various robotic techniques. In computer-assisted surgery procedures, a robotic system may be used in some surgical procedures, such as orthopedic procedures, to aid a surgeon in completing the procedures more accurately, quicker, or with less fatigue.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Systems and methods for using an augmented reality device during a surgical procedure are described herein. The systems and methods herein describe uses for the augmented reality device, such as to display a landmark or representations of real objects overlaid on a real environment. An augmented reality (AR) device allows a user to view displayed virtual objects that appear to be projected into the real environment, which is also visible. AR devices typically include two display lenses or screens, including one for each eye of a user. Light is permitted to pass through the two display lenses such that aspects of the real environment are visible while also projecting light to make virtual elements visible to the user of the AR device.

Figure 1:
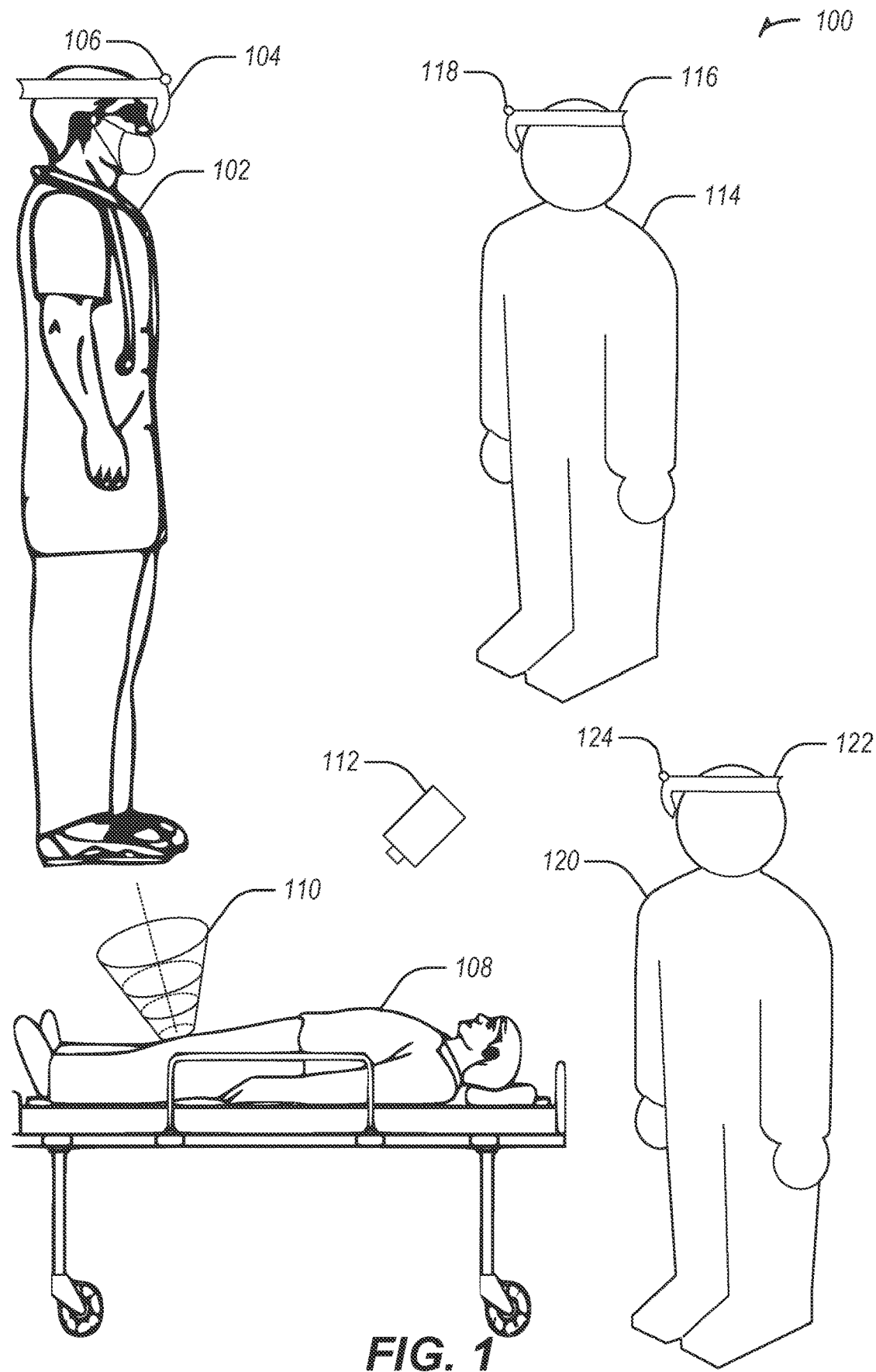
FIG. 1 illustrates surgical field in accordance with some embodiments.

FIG. 1 illustrates surgical field 100 in accordance with some embodiments. The surgical field 100 is illustrated in FIG. 1 including a surgeon 102, a patient 108, and may include a camera 112. The surgeon 102 is wearing an augmented reality (AR) device 104 which may be used to display a virtual object 110 to the surgeon 102. The virtual object 110 may not be visible to others within the surgical field 100 (e.g., surgical assistant 114 or nurse 120), though they may wear AR devices 116 and 122 respectively. Even if another person is viewing the surgical field 100 with an AR device, the person may not be able to see the virtual object 110 or may be able to see the virtual object 110 in a shared augmented reality with the surgeon 102, or may be able to see a modified version of the virtual object 110 (e.g., according to customizations unique to the surgeon 102 or the person) or may see different virtual objects entirety. Augmented reality is explained in more detail below.

Augmented reality is a technology for displaying virtual or "augmented" objects or visual effects overlaid on a real environment. The real environment may include a room or specific area (e.g., the surgical field 100), or may be more general to include the world at large. The virtual aspects overlaid on the real environment may be represented as anchored or in a set position relative to one or more aspects of the real environment. For example, the virtual object 110 may be configured to appear to be resting on a table. An AR system may present virtual aspects that are fixed to a real object without regard to a perspective of a viewer or viewers of the AR system (e.g., the surgeon 102). For example, the virtual object 110 may exist in a room, visible to a viewer of the AR system within the room and not visible to a viewer of the AR system outside the room. The virtual object 110 in the room may be displayed to the viewer outside the room when the viewer enters the room. In this example, the room may act as a real object that the virtual object 110 is fixed to in the AR system.

The AR device 104 may include one or more screens, such as a single screen or two screens (e.g., one per eye of a user). The screens may allow light to pass through the screens such that aspects of the real environment are visible while displaying the virtual object 110. The virtual object 110 may be made visible to the surgeon 102 by projecting light. The virtual object 110 may appear to have a degree of transparency or may be opaque (i.e., blocking aspects of the real environment).

An AR system may be viewable to one or more viewers, and may include differences among views available for the one or more viewers while retaining some aspects as universal among the views. For example, a heads-up display may change between two views while virtual objects may be fixed to a real object or area in both views. Aspects such as a color of an object, lighting, or other changes may be made among the views without changing a fixed position of at least one virtual object.

A user may see the virtual object 110 presented in an AR system as opaque or as including some level of transparency. In an example, the user may interact with the virtual object 110, such as by moving the virtual object 110 from a first position to a second position. For example, the user may move an object with his or her hand. This may be done in the AR system virtually by determining that the hand has moved into a position coincident or adjacent to the object (e.g., using one or more cameras, which may be mounted on an AR device, such as AR device camera 106 or separate, and which may be static or may be controlled to move), and causing the object to move in response. Virtual aspects may include virtual representations of real world objects or may include visual effects, such as lighting effects, etc. The AR system may include rules to govern the behavior of virtual objects, such as subjecting a virtual object to gravity or friction, or may include other predefined rules that defy real world physical constraints (e.g., floating objects, perpetual motion, etc.). An AR device 104 may include a camera 106 on the AR device 104 (not to be confused with the camera 112, separate from the AR device 104). The AR device camera 106 or the camera 112 may include an infrared camera, an infrared filter, a visible light filter, a plurality of cameras, a depth camera, etc. The AR device 104 may project virtual items over a representation of a real environment, which may be viewed by a user.

Eye tracking may be used with an AR system to determine which instrument a surgeon wants next by tracking the surgeon's eye to the instrument. In an example, a nurse or surgical assistant may then retrieve the determined instrument. The determined instrument may be presented in AR to the nurse or surgical assistant. In another example, the surgeon may speak the instrument (e.g., using a pre-selected code word, using speech processing and word recognition, via saying a number, or the like). The voice command may be combined with eye tracking, in still another example, to find an instrument;

The AR device 104 may be used in the surgical field 100 during a surgical procedure, for example performed by the surgeon 102 on the patient 108. The AR device 104 may project or display virtual objects, such as the virtual object 110 during the surgical procedure to augment the surgeon's vision. The surgeon 102 may control the virtual object 110 using the AR device 104, a remote controller for the AR device 104, or by interacting with the virtual object 110 (e.g., using a hand to "interact" with the virtual object 110 or a gesture recognized by the camera 106 of the AR device 104). The virtual object 108 may augment a surgical tool. For example, the virtual object 110 may appear (to the surgeon 102 viewing the virtual object 110 through the AR device 104) as a representation of a landmark previously placed on a patient bone. In another example, the virtual object 110 may be used to represent a planned location of a landmark (e.g., using a pre-operative image and a captured image of the bone in the real space). In certain examples, the virtual object 110 may react to movements of other virtual or real-world objects in the surgical field. For example, the virtual object 110 may be altered by a to move a landmark (e.g., a placed landmark). Further discussion of virtual landmarks is discussed below with respect to FIGS. 3-4.

In other examples, the virtual object 110 may be a virtual representation of a remote surgical field (e.g., an entire OR, a camera field of view of a room, a close-up view of a surgical theater, etc.). In this example, the virtual object 110 may include a plurality of virtual objects. Further discussion of this example is provided below with respect to FIGS. 5-6.

Figure 2:
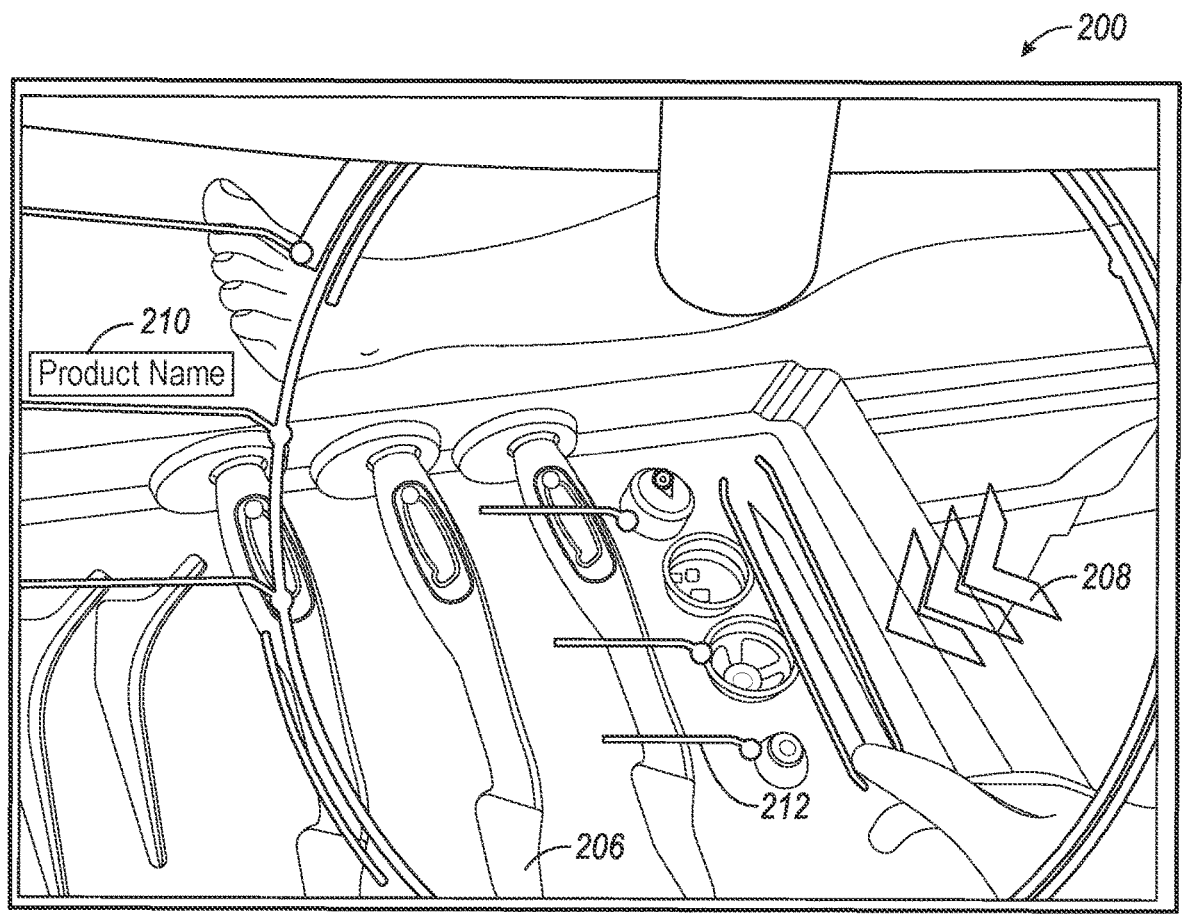
FIG. 2 illustrates an AR instrument identification display in accordance with some embodiments.

FIG. 2 illustrates an augmented reality (AR) instrument identification display 200 in accordance with some embodiments. Prior to any surgical procedure, the nursing staff unloads trays, and prepares and places instrumentation for the procedure on a table. This process may be fastidious and error prone (e.g., missing instrument, misplacement of instrument, etc.). A surgeon may have preferences for instrument placement, table location, or the like. For example, the table may be preferred in a particular setup, which may increase consistency and efficiency by removing risks of the wrong tool being picked up, which may delay a surgery. Errors due to human choice, staff change, turnover, or the like may be responsible for decreases in efficiency. The instrumentation placement process may include a check-list, which is time consuming and also error prone.

The present systems and methods may include a technological solution to errors in instrument placement by leveraging artificial intelligence or augmented reality (AR) to ensure correct placement of instruments. The systems and methods described herein may tell staff which instrument to place in what location on a table, for example based on surgeon preference (e.g., using AR). The systems and methods described herein may be used to verify that one or all instruments are correctly placed on the table, such as using an automatic check list verification. In an example, complicated instruments may be assembled using the systems and methods described herein.

The benefits of using the present systems and methods include a faster preparation or setup of a procedure room (e.g., operating room), eliminating instrument misplacement (improving workflow, efficiency, etc.), and helping avoid the need for surgeon oversight in the process.

The AR instrument identification display 200 includes a surgical instrument 206, a virtual indicator 208, and may include additional information 210, such as patient or procedure information. The virtual indicator 208 may be used to identify the surgical instrument 206 that corresponds to a procedure being performed. The virtual indicator 208 may include moving lights, flashing lights, color or changing color lights, or other virtual effects. The additional information 210 may for example, name or provide other information about the surgical instrument 206. The virtual indicator 208 may be added to the AR display 200B in response to a surgeon selection identifying a need for the surgical instrument 206. In an example, when the surgical instrument 206 is or has been moved, selected, or the surgical assistant otherwise indicates that it has been located or identified (or if the surgeon indicates it is no longer needed), the virtual indicator 208 may be removed from the AR display 200. In an example a virtual indicator 212 may be used to identify an item, such as a correctly or an incorrectly placed instrument, a verified instrument, or an unknown instrument. A user of the AR device used to present the AR display 200 may interact with the virtual indicator 208, for example by placing a finger, hand, or item adjacent to or appearing to occupy the same space as the virtual indicator 208. In response, the virtual indicator 208 may perform an action, such as displaying information about the item represented by the virtual indicator 208 (e.g., a name of the item, whether the item is a one-time use item or can be re-sterilized, whether the item is fragile, whether the item is a patient-specific or personalized item, what procedure the item is to be used for, or the like).

In an example, a schedule for procedures during a day in an operating room may be obtained or retrieved by a device. The device may provide AR capabilities to a user, including instructions for setting up a next procedure in the schedule. The users, with the aid of the AR, may place the instruments in correct position or orientation on a table in the operating room. After placement of an instrument, a verification process may be performed, and an output (e.g., correctly placed or incorrectly placed, such as with additional instructions for correct placement) may be provided to the user (e.g., via the AR). When the process is complete, and all instruments have been checked as correctly placed by the verification process, a picture may be taken and a full verification process may be performed to validate the operating room for the given procedure. The full verification process may include a second check of each instrument, a check of the instruments against needed instruments for the given procedure, timing verification based on the schedule, or the like. Data may be collected about a surgical procedure, such as a time-series of data based on progression through the procedure, what steps occur at what times (e.g., when started or completed), locations of team members (e.g., surgeon, nurse, etc.) throughout the procedure, camera stills or video of the procedure at various moments, instrument tracking or use, or the like.

Figure 3:
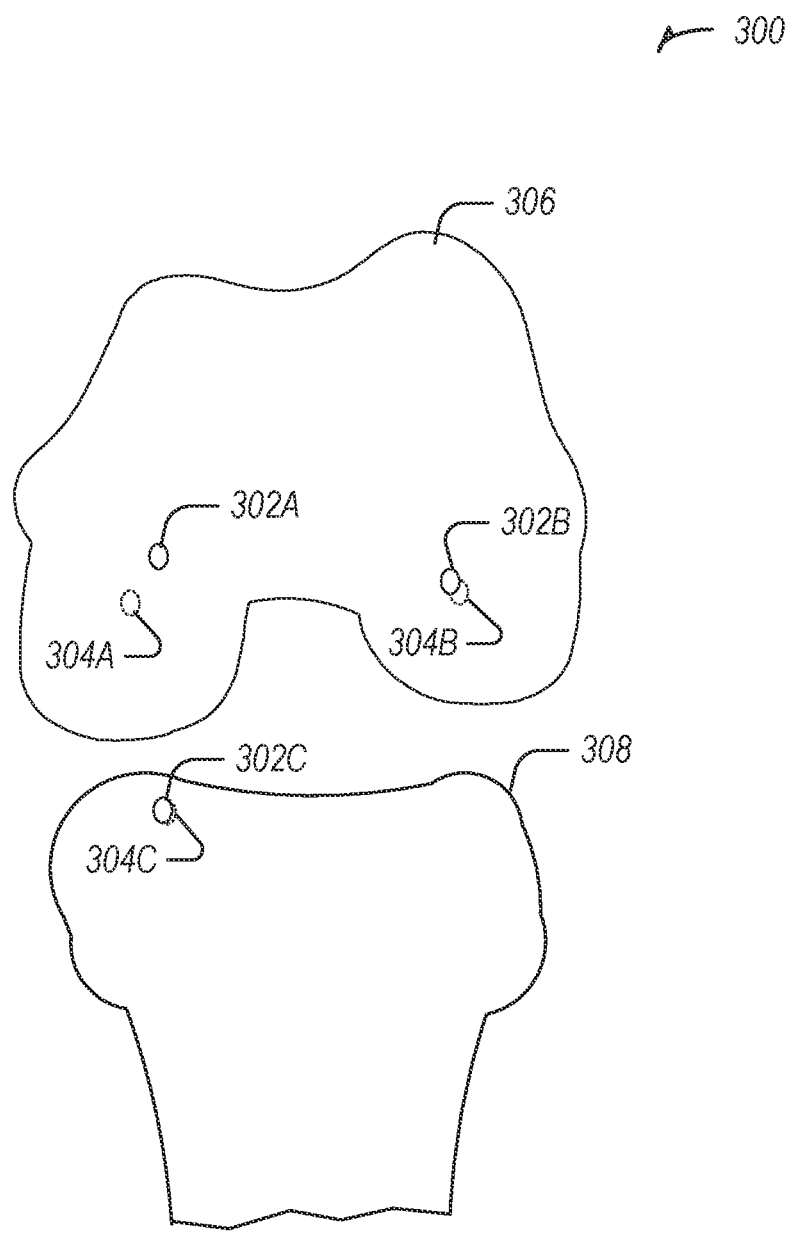
FIG. 3 illustrates a system for displaying virtual representations of a landmark in accordance with some embodiments.

FIG. 3 illustrates a system for displaying virtual representations of a landmark in accordance with some embodiments.

In an example, a landmark may be obtained, such as on a bone of a patient. An AR device may show a virtual representation of the landmark that was acquired in a display view 300. The virtual representation may be displayed on a bone (e.g., a femur 306 or a tibia 308) of the patient (e.g., overlaid on the real bone). The AR device may request confirmation (e.g., via a display) to confirm the landmark's location. In an example, a voice command may be used to control the landmark confirmation or display with the AR device.

The virtual representations may include representations of surgeon generated (e.g., selected or registered) landmarks (e.g., 302A, 302B, and 302C) or planned landmarks (e.g., 304A, 304B, and 304C). The AR display view 300 allows the femur 306 and the tibia 308 to be visible while also presenting virtual representations of landmarks. In other examples, different bones (e.g., hip, shoulder, spine, etc.) may be viewable. In still other examples, a virtual representation of a bone may be displayed with the virtual representations of landmarks (e.g., entirely virtual).

The surgeon generated landmarks may include a landmark 302A, which is displayed on the femur 306 separated by some distance from a corresponding planned landmark 304A. The planned landmark 304A may be generated based on pre-operative planning, for example using a 3D model, an image of the patient, or the like. The planned landmark 304A may be registered in the real space. For example, a known image or model coordinate system may be converted to a coordinate system in the real space using image processing. The image processing may compare captured images of a bone (e.g., in real-time), the patient, a reference object, or the like in real space to previously captured images or a previously generated model. Based on the comparison, a location of the planned landmark 304A may be registered on the real femur 306. From this registration, further processing may be used to determine how to present a virtual representation of the planned landmark 304A in the real space via an AR display device (e.g., overlaid virtually in the real space within the display view 300).

The surgeon generated landmark 302A may be registered based on an input device (e.g., a pointer that may be used to identify landmarks) or may be identified directly via the AR device (e.g., with visual processing of an indicated landmark). When using an input device, the registration to the real space for display in augmented reality may be accomplished similarly to the planned landmarks. In the case where the AR device is used to capture landmark locations directly, the location relative to the real space is known from the registration process.

The display view 300 may display only virtual representations of surgeon generated landmarks in one example, only virtual representations of planned landmarks in another example, or both in a third example. In the first example, the AR device may query the surgeon to confirm the placements (e.g., audibly, visually, etc.). In the second example, the surgeon may select virtually represented planned landmarks in the real space as surgeon generated landmarks. Said another way, the planned landmark 304A may be selected to be converted to a surgeon generated landmark, in an example. In the third example, the surgeon may be presented with an option, such as to confirm the surgeon generated landmark 302A (e.g., overriding a warning that the surgeon generated landmark 302A is some distance from the planned landmark 304A), changing the landmark location from the surgeon generated landmark 304A to the planned landmark 304A, re-doing the surgeon generated landmark 304A based on the identified distance, moving the surgeon generated landmark 304A in the direction of the planned landmark 304A (e.g., along a line or plane, or via freehand movement, such as a gesture visible within the display view 300), or the like.

The landmarks, such as 302C and 304C that are overlapping, at the same place, substantially co-located, or adjacent, may be confirmed with a single entry on a virtual user interface, via a gesture, audibly, etc., or may be skipped (e.g., not asked to confirm) and assumed to be correct. A threshold distance for different treatment may be used, and the threshold distance may be personalized, in an example. The landmarks 302B and 304B may greater than the threshold distance in some examples, but less than the threshold distance in some other examples. In some examples, only landmarks that have a distance between surgeon generated and planned greater than the threshold may trigger a warning or require confirmation input from the surgeon.

In an example, the surgeon generated landmarks may be obtained using a robotic arm, which may include an automated process, a force-assist process, a force-resist process, or the like. Even though these landmarks are referred to herein as surgeon generated, they may be obtained autonomously by the robotic arm. When using the robotic arm, the registration may leverage the coordinate system of the robotic arm to translate the landmarks to the display view 300 of the AR device (e.g., rather than or in addition to using image processing or some other technique).

A virtual navigation menu may be presented within the display view 300. The virtual navigation menu may be used to operate aspects of the robotic arm, toggle display of landmarks, proceed to a next step in a surgical procedure, or the like. The navigation menu may be moved or resized within the display view 300, in an example. Movement may occur in response to a gesture, audible instruction, or the like. In an example, the virtual navigation menu may automatically and virtually follow the robotic arm moving in real space, such as within the display view 300.

Figure 4:
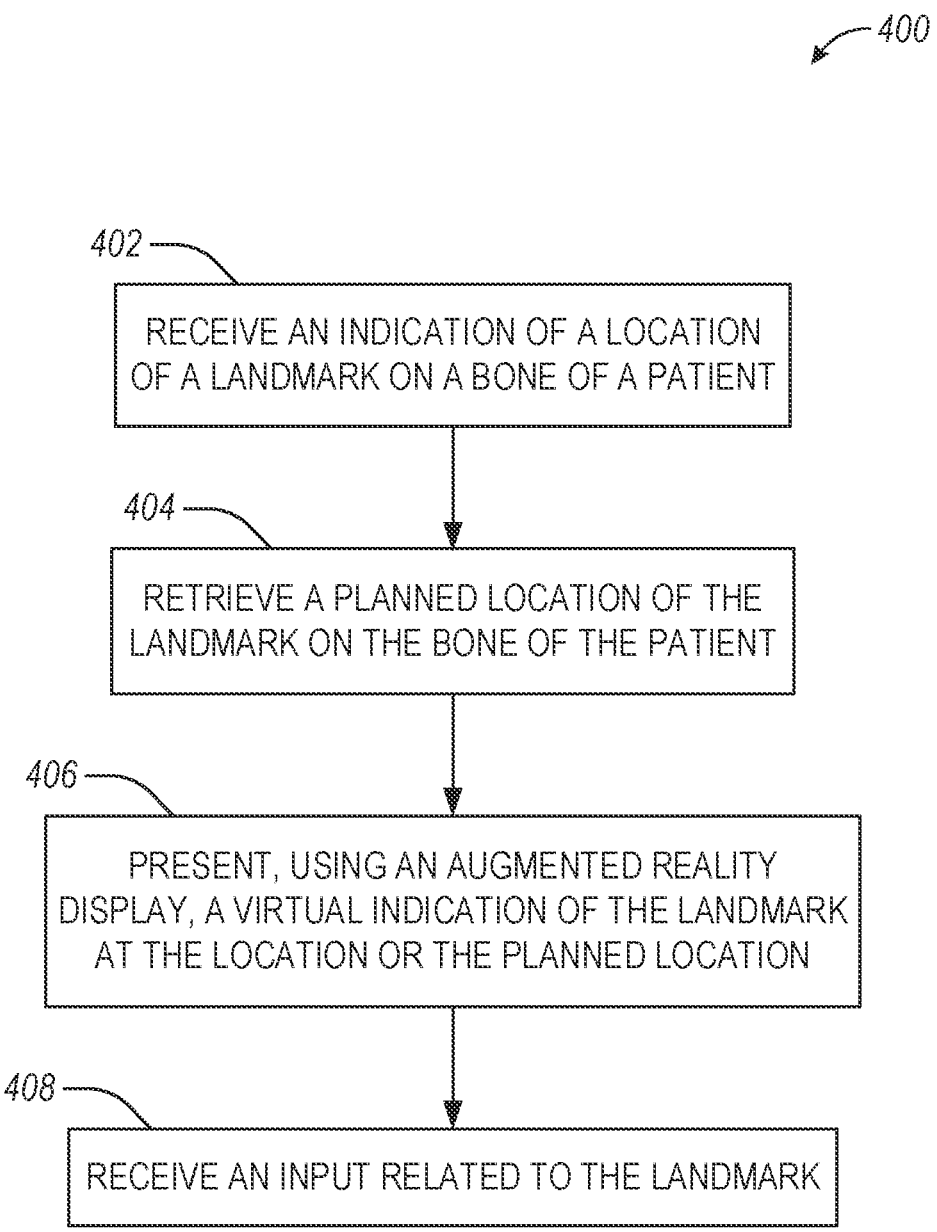
FIG. 4 illustrates a flowchart showing a technique for displaying virtual representations of a landmark in accordance with some embodiments.

FIG. 4 illustrates a flowchart showing a technique 400 for displaying virtual representations of a landmark in accordance with some embodiments. The technique 400 may be performed by a processor, for example by executing instructions stored in memory.

The technique 400 includes an operation 402 to receive an indication of a location of a landmark on a bone of a patient. The indication may be stored in a database or received directly from a landmark generation device (e.g., a pointer). The technique 400 may include registering the bone using a 3D model before receiving the indication of the landmark. A position or orientation of the bone may be determined using bone tracking, such as via a passive robotic arm.

The technique 400 includes an operation 404 to retrieve a planned location of the landmark on the bone of the patient. The planned location may be retrieved based on a pre-operative image of the bone of the patient. The pre-operative image may be registered to a current patient space, in an example.

The technique 400 includes an operation 406 to present, using an augmented reality display, a virtual indication of the landmark at the location or the planned location, or both. The virtual indication may be presented within a surgical field while permitting the surgical field to be viewed through the augmented reality display.

The technique 400 includes an operation 408 to receive an input related to the landmark. The input may include a response to a request for confirmation of the location of the landmark. Operation 408 may include moving the location, confirming the location, indicating that the location is to be re-selected, validating the location, temporarily accepting or denying the location, an indication to remove the virtual indication (which may then be removed), or the like.

The technique 400 may include displaying a virtual navigation menu in the augmented reality display. A user may virtually interact with the virtual navigation menu as if it was displayed on a screen. An indication may be received to move the virtual navigation menu presented in the augmented reality display, for example to make the location more convenient. The technique 400 may include displaying a live video, using the augmented reality display, of the bone using a camera affixed to an end effector of a robotic arm.

Figure 5:
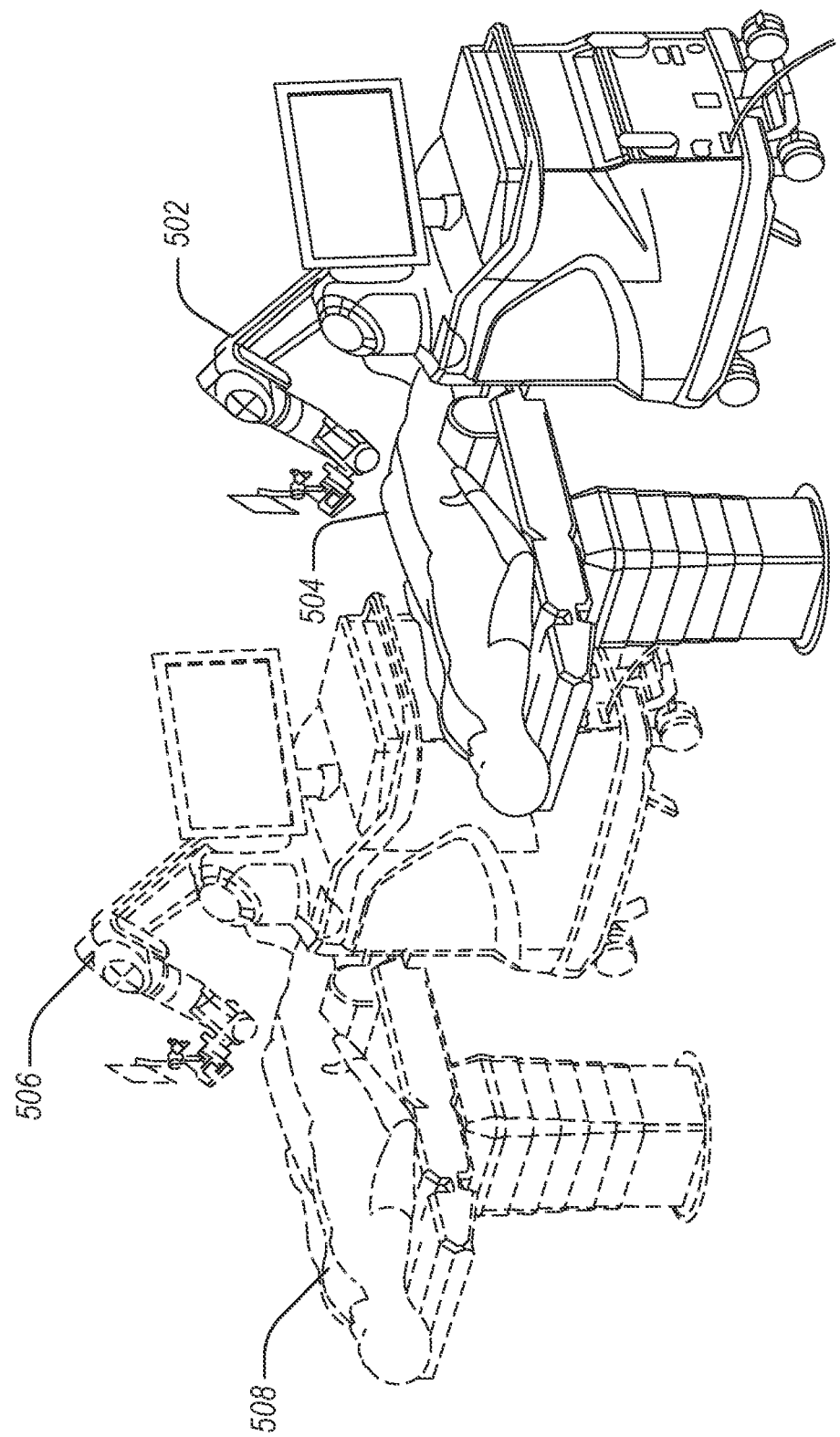
FIG. 5 illustrates a surgical field including a virtual representation of a remote surgical field, for example for use with an augmented reality display in accordance with some embodiments.

FIG. 5 illustrates a surgical field including a virtual representation of a remote surgical field, for example for use with an augmented reality display in accordance with some embodiments. The surgical field may be viewable within a display view 500 of an AR device. The AR device may show a virtual representation of the remote surgical field. In an example, a voice command or gesture may be used to control whether the remote surgical field is viewable or not.

The display view 500 may be configured to display aspects of the remote surgical field, such as a remote patient 508 or a remote robotic arm 506, displayed in full or zoomed in, such as according to surgeon preference or control. For example, the display view 500 may include a close-up view of a leg or bone of the remote patient 508, for example during a surgical procedure.

The display view 500 presents a virtual representation of an aspect of the remote surgical field while permitting a local real surgical field to be displayed. The real surgical field may include a patient 504 or a robotic arm 502, in some examples. The virtual representation may be displayed adjacent to the patient 504, the robotic arm 502, or elsewhere within the local real surgical field. Adjacent in this context may include separated by an absolute distance within the surgical field, separated by a perceived distance (e.g., appearing in the display view 500 to be separated by a foot, a few feet, etc.), anchored in a location (e.g., virtually displayed at a real location within the local surgical field), or moved according to surgeon preference. In some examples, the virtual representation may move when zoomed in or out. For example, when only a leg of the remote patient 508 is virtually visible, the leg may be placed closer to the real leg of the patient 504, but when the patient 508 is viewed in full, this distance may be increased. The virtual representation of the remote surgical field may be based on images (e.g., video) captured by a camera affixed to the remote robotic arm 506. For example, the camera on the remote robotic arm 506 may identify a feature, and another camera or an AR device in the remote surgical field may be used to see different points of view (e.g., camera views).

In an example, the remote patient 508 is a live surgical patient and the local patient 504 is a live surgical patient. In this example, the remote patient 508 may be remotely operated on using the robotic arm 506 by a surgeon in the real space of the display view 500. For example, the surgeon may simultaneously operate on both the remote patient 508 and the local patient 504. Simultaneously in this example may mean the surgeon switches between the patients at various operations of the surgery, such as at each step or after particular sequences of steps, or one surgery may be completed before the next is started, but both patients are available, viewable, or ready for surgery contemporaneously. In this version of this example, the surgeon may complete surgeries more quickly because multiple staff, operating rooms, and surgical equipment may be used in parallel rather than requiring serial surgeries. In another version of this example, the remote patient 508 may be operated on by a remote surgeon (e.g., with or without the use of the robotic arm 506), and the surgeon in the local space of the display view 500 may be called in to consult or provide assistance (e.g., with a portion of a procedure, such as operation of the remote robotic arm 506, for example when the remote surgeon is less experienced using a robotic arm). The remote patient 508 is viewable for the consultation (e.g., in real-time) such that the surgeon in the local space may give direction or advise without needing to physically leave the local surgical field. This version of the example may be particularly useful when the remote surgeon is a student, a newer surgeon, or the surgery is occurring in a remote building, city, country, etc.

In an example, the remote patient 508 is a live surgical patient and the local patient 504 is a cadaver. In this example, a surgeon in local space 500 may view a remote surgery, which may be occurring in real-time or may have already occurred and is viewed on replay. This example allows for a student or newer surgeon to complete a procedure (e.g., a new type or particularly difficult type) on a cadaver while being able to view a similar or the same procedure virtually. The virtual representation may be viewed at different angles, zoomed, or the like. When the virtual representation is a replay, the surgery may be reversed, sped up, paused, etc. In another version of this example, a remote surgeon may request advice or support from the local surgeon, who may attempt a portion of the surgery on the cadaver before the portion is attempted on the live remote patient 508. This allows for the portion of the procedure to be tested without damage to the live remote patient 508.

In an example, the remote patient 508 is a cadaver and the local patient 504 is a live surgical patient. In this example, a surgeon in the local space of the display view 500 may attempt a portion of a procedure on the remote cadaver before attempting the portion on the live local patient 504. The local surgeon may control the remote robotic arm 506 while performing the portion on the cadaver. The remote robotic arm 506 may save actions undertaken during the operation, which may be sent to the local robotic arm 502, and optionally edited. The saved actions may be repeated by the local robotic arm 502, for example to perform an autonomous portion of the procedure that has been tested on the cadaver. Differences between the cadaver and the local live patient 504 may be used to alter the saved actions, for example by scaling, moving target points, or the like. Differences in the robotic arms may be accounted for based on a calibration step performed before starting the surgical procedure. In an example, a procedure may be tested on a cadaver using the remote robotic arm 506, then successful actions may be transferred to the local robotic arm 502 for autonomous action or force-resist type movement by the local robotic arm 502 when performing the procedure on the local patient 504.

In an example, the remote patient 508 is a cadaver and the local patient 504 is a cadaver. In this example, a surgeon may practice a procedure on two different cadavers contemporaneously to identify differences in results from changes to the procedure. In another version of this example, the surgeon may perform a procedure for a student or newer surgeon while the student or newer surgeon operates remotely on the cadaver. In this version, the local surgeon may view and optionally critique the remote surgery. The remote surgical field may have a similar setup, allowing the student or newer surgeon to view the teaching surgeon's operation in an augmented or virtual reality view.

In any of the above examples, more than one remote surgical field may be presented. For example, a teaching surgeon may view multiple remote student surgeries. When two or more remote surgical fields are presented, they may be scaled to fit in the display view 500. A remote surgical field may be placed adjacent another remote surgical field, in an example.

A local surgeon may provide assistance when requested for a remote procedure, such as in a collaborative mode with the remote surgical arm 506. The collaborative mode may allow the local surgeon to move the remote surgical arm 506, while allowing the remote surgeon to stop the remote surgical arm 506. In another example, the local surgeon may be stop or take over control of the remote surgical arm 506 while monitoring the remote surgeon operating with the remote surgical arm 506. In yet another example, the local surgeon may control the local robotic arm 502, which in turn may send information to control the remote robotic arm 506 or the local robotic arm 502 may move in response to information received from the remote robotic arm 506. For example, the robotic arms may move in concert, such that either the remote or local surgeon may control the procedure. One of the surgeons may act to resist erroneous movements while the other of the surgeons performs the procedure, each using their respective robotic arm. In an example, the remote surgical field may represent a surgical field in a same building as the local surgical field.

Figure 6:
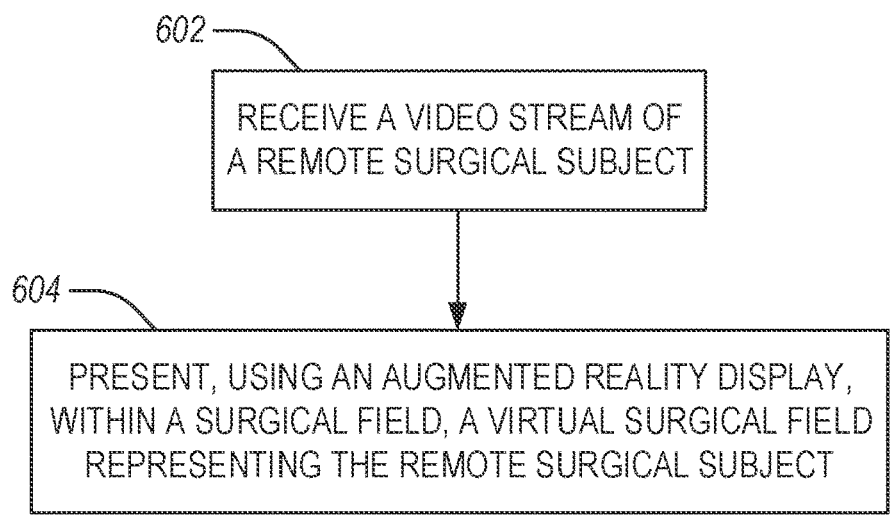
FIG. 6 illustrates a flowchart showing a technique for displaying a virtual representation of a remote surgical field within a local surgical field in accordance with some embodiments.

FIG. 6 illustrates a flowchart showing a technique 600 for displaying a virtual representation of a remote surgical field within a local surgical field in accordance with some embodiments. The technique 600 may be performed by a processor, for example by executing instructions stored in memory. The technique 600 includes an operation 602 to receive a video stream of a remote surgical subject.

The technique 600 includes an operation 604 to present, using an augmented reality display, within a surgical field, a virtual surgical field representing the remote surgical subject. Operation 604 may include presenting the virtual surgical field while permitting a patient within the surgical field to be viewed through the augmented reality device. The virtual surgical field may be presented adjacent to the patient, in an example. Adjacent may mean separated by a fixed distance in absolute space within the surgical field, for example a foot, a few feet, etc. In another example, adjacent may mean separated by a relative distance as perceived through the augmented reality device (e.g., appearing to be separated by a foot, a few feet, etc.). Adjacent may mean touching, or almost touching.

The remote surgical subject may include a patient in another operating room within a building also housing the surgical field, a cadaver, or the like. The technique 600 may further include an operation to receive a voice instruction and send the voice instruction to a remote speaker (e.g., within a remote surgical field corresponding to and represented by the virtual surgical field). The technique 600 may include receiving a request to present the virtual surgical field before presenting the virtual surgical field (e.g., from a colleague, student, etc.). The virtual surgical field may be used for testing aspects of a technique (e.g., with a cadaver), for helping or consulting on a case, or to perform an entire procedure, in various examples. A second virtual surgical field may be presented (e.g., adjacent to the patient, such as on an opposite side, or adjacent to the first surgical field) for interaction or observation of a second remote surgical subject.

The virtual surgical field may be displayed including a virtual representation of a remote surgical robot. The remote surgical robot may be controlled by a command issued within the surgical field, for example via a voice command, a gesture, a user input on a device, touchscreen, virtual indication, a written, typed, haptic command, or the like. The remote surgical robot may be guided via a gesture. In an example, the virtual surgical field may be displayed based on output of a camera affixed to an end effector of the remote surgical robot.

Figure 7:
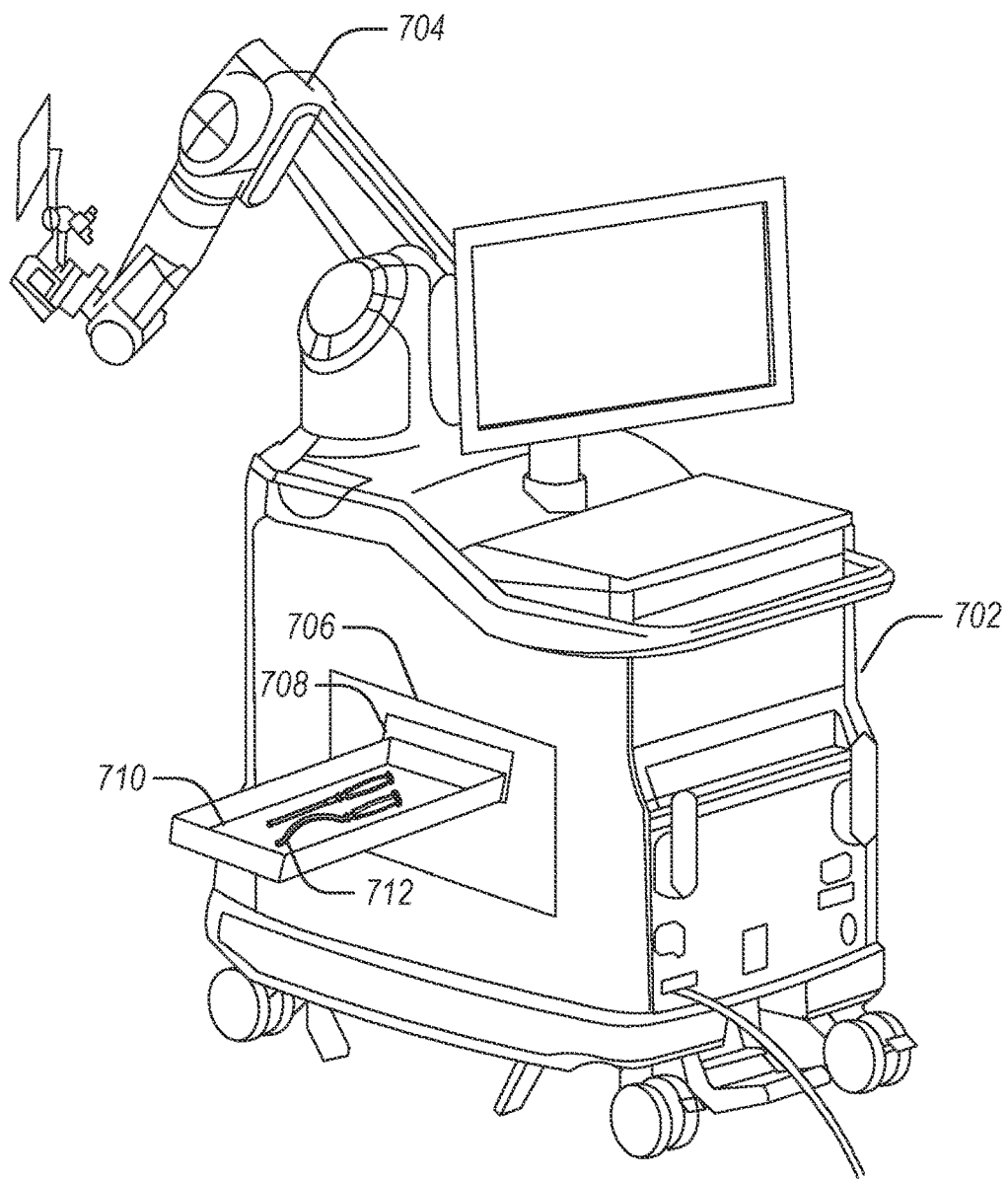
FIG. 7 illustrates a robot sterilization system in accordance with some embodiments.

FIG. 7 illustrates a robot sterilization system 700 in accordance with some embodiments. The robot sterilization system 700 includes a robotic arm 704, and a sterilization unit 706, which may be embedded in a base 702 of the robotic arm 704 or may be separate from the robotic arm 704. When separate, the sterilization unit 706 may be mounted under the robotic arm 704 or affixed to a portion of the robotic arm 704 (e.g., the base 702).

The sterilization unit 706 may include an opening 708 that may be used to output an instrument (e.g., instrument 712). In an example, an instrument may be output from the opening 708, for example using a mechanism within the sterilization unit 706. In another example, the sterilization unit 706 may include a tray 710, which may be output from the opening 708, the tray 710 used to convey the instrument 712. In yet another example, a door of the sterilization unit 706 may open to allow a user to remote an instrument. In still another example, the robotic arm 704 may be used to retrieve an instrument from within the sterilization unit 706. For example, the robotic arm 704 may retrieve an instrument from within the sterilization unit 706 based on known locations of instruments within the sterilization unit 706.

A door may be used to reload the sterilization unit 706 in an example. The sterilization unit 706 may include a sterile environment without the capability of sterilizing instruments. In this example, the sterilization unit 706 is a passive sterile storage unit. In another example, the sterilization unit 706 may be used to sterilize an instrument. In this example, the sterilization unit 706 may use sterilization equipment to sterilize the instrument, such as by using ultraviolet light, steam, gas, an autoclave, alcohol, heat pressure, glass beads, or the like.

The sterilization unit 706 may be controlled by a user interface or control mechanism, such as one incorporated in the base 702 or one also used to control the robotic arm 704 (e.g., an augmented reality user interface, a display screen, a microphone and algorithm for interpreting audible commands, the robotic arm 704 itself, or the like). Controls may include initiating sterilization of an instrument (or all instruments within he sterilization unit 706) or outputting an instrument (e.g., opening a door, outputting a specific selected instrument, outputting a next instrument in a procedure, or outputting a machine learning model identified instrument at a particular step in a procedure).

The instrument 712 may be output automatically, for example based on surgeon preferences, a machine learned model, or the like. For example, image processing may be used to determine a step of a procedure that is completed or almost completed, and an instrument for a next step may be output. In another example, movement of the robotic arm 704 may be used to determine that an instrument is needed and output that instrument. In this example, the movement may be a stored movement or a movement unique to a portion of a surgical procedure that identifies a next step. In an example, the instrument 712 is adapted to connect to an end effector of the surgical robotic system (e.g., where the end effector is affixed to a distal end of the surgical robotic arm).

In an example, the surgical robotic system stores, or is connected to a database that stores, a schedule of upcoming cases, events, procedures, etc. These cases, events, procedures, etc., may be related to a particular patient, particular surgeon, the instrument 712, a surgical room, the robot sterilization system 700, or the like. The robot sterilization system 700 may include a processor, such as for use with a robotic control device to control movement of the robotic arm 704, the sterilization unit 706, etc. In an example, the processor may identify that the instrument 712 is to be used in an upcoming procedure, and determine whether the instrument 712 is currently in a sterilized state. In response to determining that the instrument 712 is not in a sterilized state, the processor may schedule a sterilization process for the instrument 712 to occur before the upcoming procedure. For example, a sterilization of the instrument may be performed during scheduled downtown, before an upcoming case, event, or procedure, or during off hours or unscheduled time. In some examples, the processor may schedule time for the sterilization.

Figure 8:
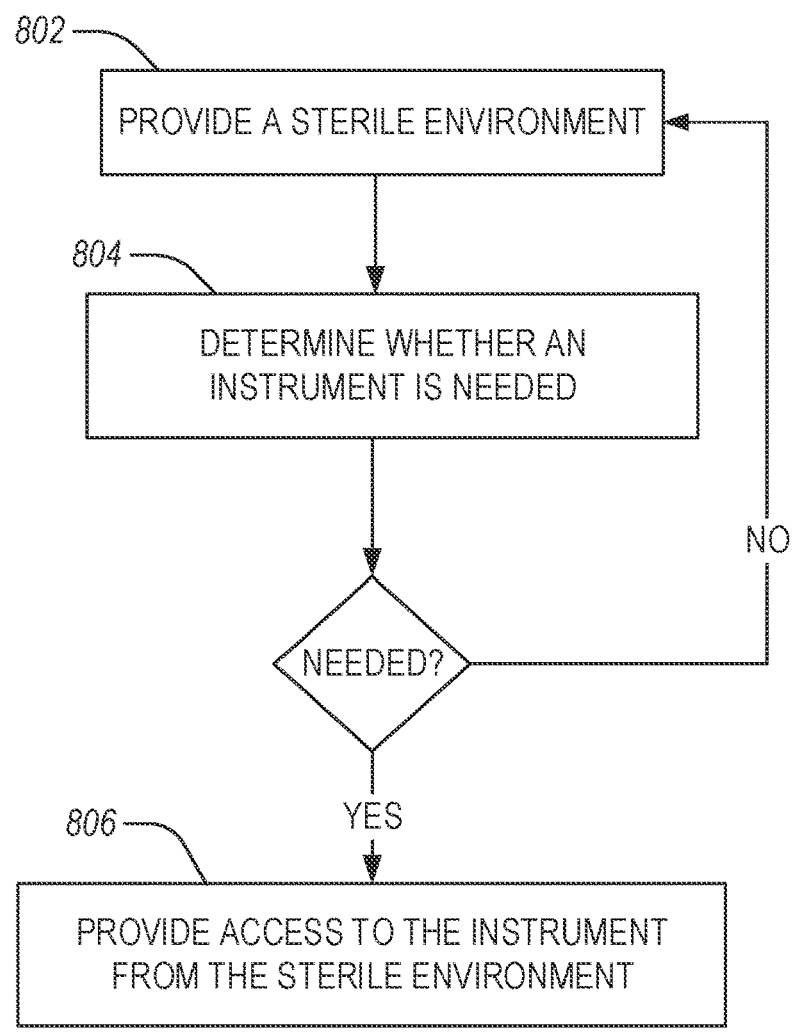
FIG. 8 illustrates a flowchart showing a technique for storing a sterilized instrument using a robotic system in accordance with some embodiments.

FIG. 8 illustrates a flowchart showing a technique 800 for storing a sterilized instrument using a robotic system in accordance with some embodiments. The technique 800 may be implemented using a surgical robotic system, such as with a processor.

The technique 800 includes an operation 802 to provide a sterile environment. The sterile environment may be housed by a sterilization unit to store an instrument. The sterilization unit may be mounted under or form a base of a surgical robotic arm of the surgical robotic system. In the example where the sterilization unit is mounted under the surgical robotic arm, the sterilization unit may be a portable sterilization unit. In an example, the sterilization unit may be a sterile storage unit without sterilization capabilities itself in another example, the sterilization unit may be configured to actively sterilize the instrument, for example using ultraviolet light, steam, gas, an autoclave, alcohol, heat pressure, glass beads, or the like. The sterilization unit may store a plurality of instruments including the instrument.

The technique 800 includes an operation 804 to determine whether the instrument is needed. In response to a determination that the instrument is not needed, the technique 800 may return to operation 602 or 604. Operation 804 may include using machine learning techniques to determine that the instrument is needed. For example, a trained model (which may include a binary classification, a regression model, a convolutional neural network, etc.) may be used to determine that a surgical step has been reached, that a time has passed, previously stored surgeon preferences, probability, a selected workflow, or the like. In other examples, a command, such as a spoken command, a gesture, an interaction with a physical or virtual user interface, or other techniques may be used to determine that the instrument is needed (e.g., a request for the instrument).

The technique 800 includes an operation 806 to, in response to a determination that the instrument is needed, provide access to the instrument from the sterile environment. Operation 806 may include displaying an indication of the instrument using an augmented reality display device. Operation 806 may include causing an enclosure of the sterilization unit to open, exposing the sterile environment including the instrument. Operation 806 may include causing the surgical robotic arm to retrieve the instrument. Operation 806 may include causing the instrument to be output from the sterilization unit via a mechanical conveyance. Operation 806 may include providing a set of sterile instruments, including the instrument, for a procedure.

Figure 9:
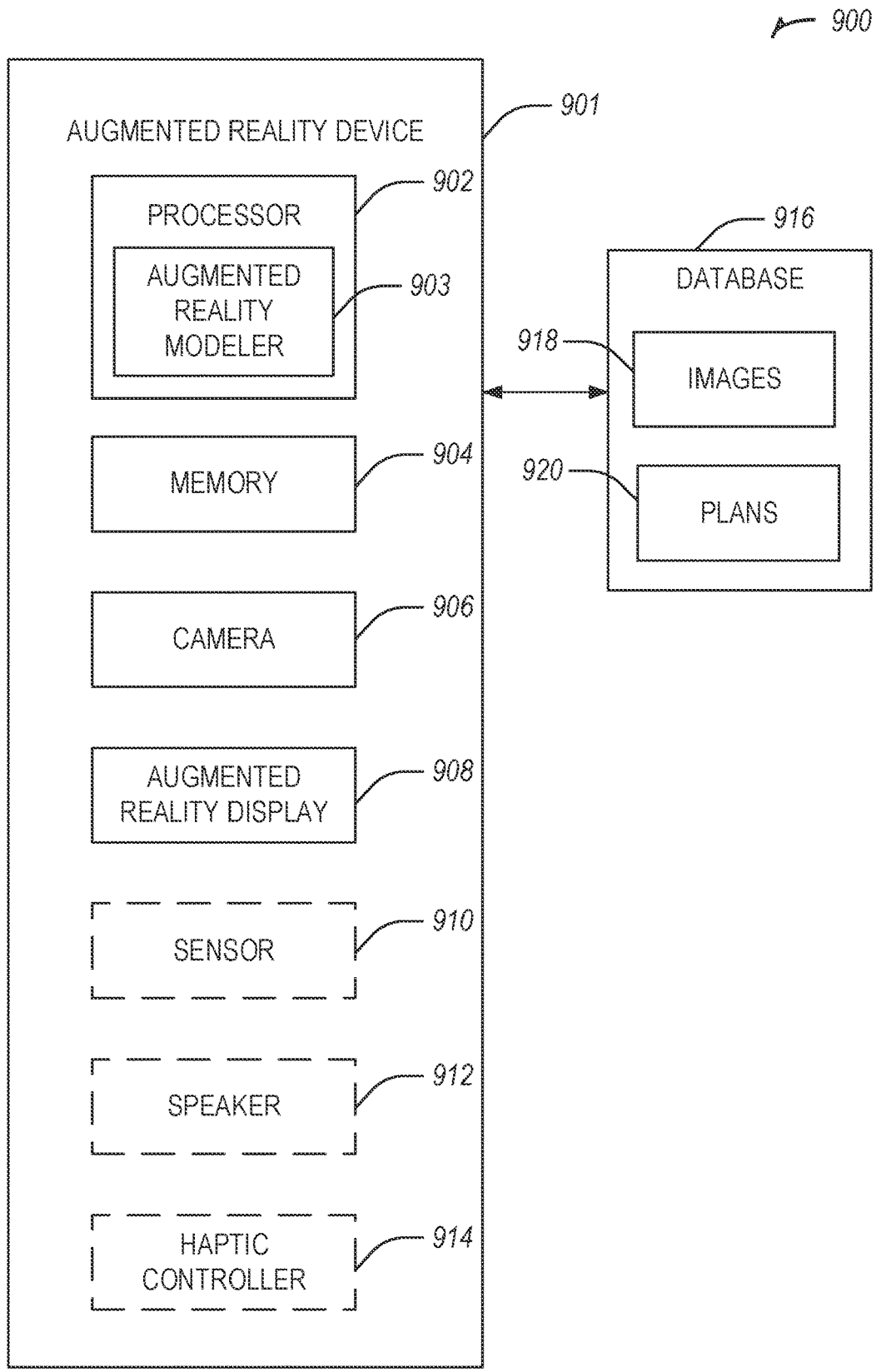
FIG. 9 illustrates a system for surgical instrument identification using an augmented reality display in accordance with some embodiments.

FIG. 9 illustrates a system 900 for surgical instrument identification using an augmented reality display in accordance with some embodiments. The system 900 may be used to perform any of the techniques 400 or 600 described in relation to FIG. 4 or 6, for example, by using a processor 902. The system 900 includes an augmented reality device 901 that may be in communication with a database 916. The augmented reality device 901 includes a processor 902, memory 904, an AR display 908, and a camera 906. The augmented reality device 901 may include a sensor 910, a speaker 912, or a haptic controller 914. The database 916 may include image storage 918 or preoperative plan storage 920. In an example, the augmented reality device 901 may be a HoloLens manufactured by Microsoft of Redmond, Washington.

The processor 902 of the augmented reality device 901 includes an augmented reality modeler 903. The augmented reality modeler 903 may be used by the processor 902 to create the augmented reality environment. For example, the augmented reality modeler 903 may receive dimensions of a room, such as from the camera 906 or sensor 910, and create the augmented reality environment to fit within the physical structure of the room. In another example, physical objects may be present in the room and the augmented reality modeler 903 may use the physical objects to present virtual objects in the augmented reality environment. For example, the augmented reality modeler 903 may use or detect a table present in the room and present a virtual object as resting on the table. The AR display 908 may display the AR environment overlaid on a real environment. The display 908 may show a virtual object, using the AR device 901, such as in a fixed position in the AR environment. The augmented reality modeler 903 may receive a video stream of a remote surgical field for virtually displaying within the room. In an example, a dimension of a virtual object (e.g., a remote surgical field) may be modified (e.g., shrunk) to be virtually displayed within the room. In an example, the augmented reality device 901 may provide a zoom function to allow a user to zoom in on a portion of a virtual object (e.g., within a virtual surgical field).

The augmented reality device 901 may include a sensor 910, such as an infrared sensor. The camera 906 or the sensor 910 may be used to detect movement, such as a gesture by a surgeon or other user, that may be interpreted by the processor 902 as attempted or intended interaction by the user with the virtual target. The processor 902 may identify an object in a real environment, such as through processing information received using the camera 906.

The AR display 908, for example during a surgical procedure, may present, such as within a surgical field while permitting the surgical field to be viewed through the augmented reality display, a virtual feature corresponding to a physical feature hidden by an anatomical aspect of a patient. The virtual feature may have a virtual position or orientation corresponding to a first physical position or orientation of the physical feature. In an example, the virtual position or orientation of the virtual feature may include an offset from the first physical position or orientation of the physical feature. The offset may include a predetermined distance from the augmented reality display, a relative distance from the augmented reality display to the anatomical aspect, or the like.

Figure 10:
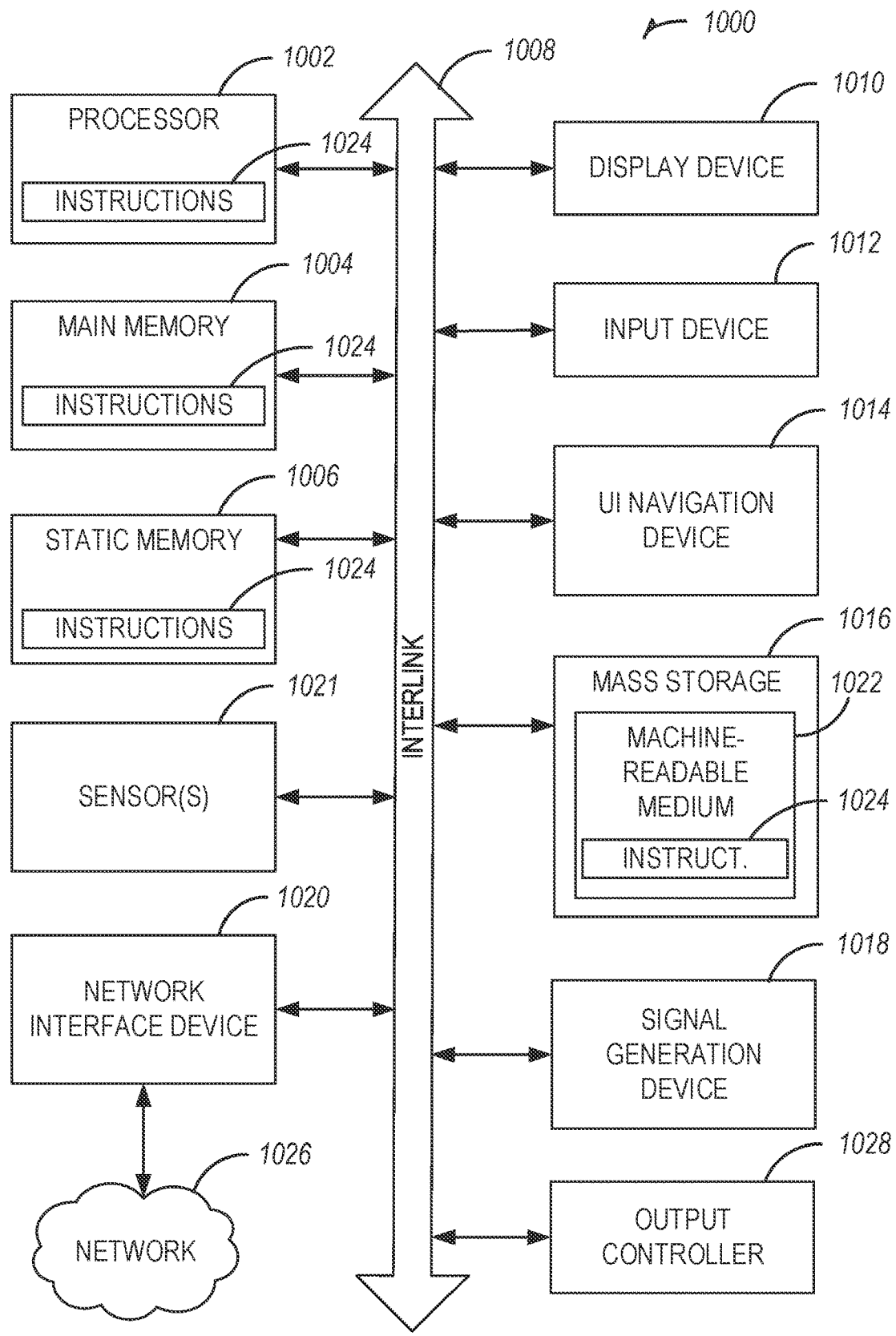
FIG. 10 illustrates generally an example of a block diagram of a machine upon which any one or more of the techniques discussed herein may perform in accordance with some embodiments.

FIG. 10 illustrates generally an example of a block diagram of a machine 1000 upon which any one or more of the techniques (e.g., methodologies) discussed herein may perform in accordance with some embodiments. In alternative embodiments, the machine 1000 may operate as a standalone device or may be connected (e.g., networked) to other machines. In a networked deployment, the machine 1000 may operate in the capacity of a server machine, a client machine, or both in server-client network environments. The machine 1000 may be a personal computer (PC), a tablet PC, a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or like mechanisms. Such mechanisms are tangible entities (e.g., hardware) capable of performing specified operations when operating. In an example, the hardware may be specifically configured to carry out a specific operation (e.g., hardwired). In an example, the hardware may include configurable execution units (e.g., transistors, circuits, etc.) and a computer readable medium containing instructions, where the instructions configure the execution units to carry out a specific operation when in operation. The configuring may occur under the direction of the executions units or a loading mechanism. Accordingly, the execution units are communicatively coupled to the computer readable medium when the device is operating. For example, under operation, the execution units may be configured by a first set of instructions to implement a first set of features at one point in time and reconfigured by a second set of instructions to implement a second set of features.

Machine (e.g., computer system) 1000 may include a hardware processor 1002 (e.g., a central processing unit (CPU), a graphics processing unit (GPU), a hardware processor core, or any combination thereof), a main memory 1004 and a static memory 1006, some or all of which may communicate with each other via an interlink (e.g., bus) 1008. The machine 1000 may further include a display unit 1010, an alphanumeric input device 1012 (e.g., a keyboard), and a user interface (UT) navigation device 1014 (e.g., a mouse). In an example, the display unit 1010, alphanumeric input device 1012 and UT navigation device 1014 may be a touch screen display. The display unit 1010 may include goggles, glasses, or other AR or VR display components. For example, the display unit may be worn on a head of a user and may provide a heads-up-display to the user. The alphanumeric input device 1012 may include a virtual keyboard (e.g., a keyboard displayed virtually in a VR or AR setting.

The machine 1000 may additionally include a storage device (e.g., drive unit) 1016, a signal generation device 1018 (e.g., a speaker), a network interface device 1020, and one or more sensors 1021, such as a global positioning system (GPS) sensor, compass, accelerometer, or other sensor. The machine 1000 may include an output controller 1028, such as a serial (e.g., universal serial bus (USB), parallel, or other wired or wireless (e.g., infrared (IR), near field communication (NFC), etc.) connection to communicate or control one or more peripheral devices.

The storage device 1016 may include a machine readable medium 1022 that is non-transitory on which is stored one or more sets of data structures or instructions 1024 (e.g., software) embodying or utilized by any one or more of the techniques or functions described herein. The instructions 1024 may also reside, completely or at least partially, within the main memory 1004, within static memory 1006, or within the hardware processor 1002 during execution thereof by the machine 1000. In an example, one or any combination of the hardware processor 1002, the main memory 1004, the static memory 1006, or the storage device 1016 may constitute machine readable media.

While the machine readable medium 1022 is illustrated as a single medium, the term "machine readable medium" may include a single medium or multiple media (e.g., a centralized or distributed database, or associated caches and servers) configured to store the one or more instructions 1024.

The term "machine readable medium" may include any medium that is capable of storing, encoding, or carrying instructions for execution by the machine 1000 and that cause the machine 1000 to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1024 may further be transmitted or received over a communications network 1026 using a transmission medium via the network interface device 1020 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, as the personal area network family of standards known as Bluetooth® that are promulgated by the Bluetooth Special Interest Group, peer-to-peer (P2P) networks, among others. In an example, the network interface device 1020 may include one or more physical jacks (e.g., Ethernet, coaxial, or phone jacks) or one or more antennas to connect to the communications network 1026. In an example, the network interface device 1020 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1000, and includes digital or analog communications signals or other intangible medium to facilitate communication of such software.

Example 1 is a method for using an augmented reality device in a surgical field comprising: receiving, at a processor, an indication of a location of a landmark on a bone of a patient; retrieving, using the processor, a planned location of the landmark on the bone of the patient based on a pre-operative image of the bone of the patient; presenting, using an augmented reality display, within a surgical field, while permitting the surgical field to be viewed through the augmented reality display, a virtual indication of the landmark at the location and a virtual indication of the landmark at the planned location; and receiving, at the processor, a response to a request for confirmation of the location of the landmark.

In Example 2, the subject matter of Example 1 includes, wherein the indication of the location of the landmark is stored in a database.

In Example 3, the subject matter of Examples 1-2 includes, wherein the indication of the location of the landmark is received directly from a landmark generation device.

In Example 4, the subject matter of Examples 1-3 includes, wherein the response confirms the location of the landmark.

In Example 5, the subject matter of Examples 1-4 includes, wherein the response changes the location of the landmark to the planned location.

In Example 6, the subject matter of Examples 1-5 includes, wherein the response includes a new location for the landmark.

In Example 7, the subject matter of Examples 1-6 includes, removing the virtual indication in response to receiving the response.

In Example 8, the subject matter of Examples 1-7 includes, registering the bone using a 3D model before receiving the indication of the landmark.

In Example 9, the subject matter of Examples 1-8 includes, receiving an indication to move a virtual navigation menu presented in the augmented reality display.

In Example 10, the subject matter of Examples 1-9 includes, wherein a position and orientation of the bone is determined using bone tracking via a passive robotic arm.

In Example 11, the subject matter of Examples 1-10 includes, displaying a live video, using the augmented reality display, of the bone using a camera affixed to an end effector of a robotic arm.

Example 12 is a system configured to perform operations of any of any of the methods of Examples 1-11.

Example 13 is at least one machine-readable medium including instructions for operation of a computing system, which when executed by a machine, cause the machine to perform operations of any of the methods of Examples 1-11.

Example 14 is an apparatus comprising means for performing any of the methods of Examples 1-11.

Example 15 is a method for using an augmented reality device in a surgical field comprising: receiving a video stream of a remote surgical subject; and presenting, using an augmented reality display, within a surgical field, while permitting a patient within the surgical field to be viewed through the augmented reality display, a virtual surgical field adjacent to the patient, the virtual surgical field representing the remote surgical subject.

In Example 16, the subject matter of Example 15 includes, receiving a voice instruction and sending the voice instruction to a remote speaker.

In Example 17, the subject matter of Examples 15-16 includes, wherein the remote surgical subject includes a patient in another operating room within a building housing the surgical field.

In Example 18, the subject matter of Examples 15-17 includes, wherein the remote surgical subject includes a cadaver.

In Example 19, the subject matter of Examples 15-18 includes, wherein presenting the virtual surgical field includes displaying a virtual representation of a remote surgical robot.

In Example 20, the subject matter of Example 19 includes, sending a command to the remote surgical robot.

In Example 21, the subject matter of Example 20 includes, wherein the command includes a written, typed, touchscreen-selected, augmented reality selected, or spoken command.

In Example 22, the subject matter of Examples 19-21 includes, guiding the remote surgical robot via a gesture.

In Example 23, the subject matter of Examples 19-22 includes, displaying a view of the virtual surgical field using a camera affixed to an end effector of the remote surgical robot.

In Example 24, the subject matter of Examples 15-23 includes, receiving a request to present the virtual surgical field before presenting the virtual surgical field.

In Example 25, the subject matter of Examples 15-24 includes, presenting a second virtual surgical field adjacent to the patient or adjacent to the virtual surgical field, the second virtual surgical field representing a second remote surgical subject.

Example 26 is a system configured to perform operations of any of any of the methods of Examples 15-25.

Example 27 is at least one machine-readable medium including instructions for operation of a computing system, which when executed by a machine, cause the machine to perform operations of any of the methods of Examples 15-25.

Example 28 is an apparatus comprising means for performing any of the methods of Examples 15-25.

Example 29 is a surgical robotic system comprising: a surgical robotic arm; a sterilization unit enclosing a sterile environment and storing an instrument; a processor configured to: determine that the instrument is needed in an upcoming portion of a surgical procedure; and provide access to the instrument.

In Example 30, the subject matter of Example 29 includes, wherein the sterilization unit is a base of the surgical robotic arm.

In Example 31, the subject matter of Examples 29-30 includes, wherein the sterilization unit is a portable sterilization unit, and wherein the surgical robotic arm is configured to be mounted on the portable sterilization unit.

In Example 32, the subject matter of Examples 29-31 includes, wherein the sterilization unit is a sterile storage unit without sterilization capabilities.

In Example 33, the subject matter of Examples 29-32 includes, wherein the sterilization unit is configured to actively sterilize the instrument.

In Example 34, the subject matter of Examples 29-33 includes, wherein the sterilization unit is configured to store a plurality of instruments including the instrument.

In Example 35, the subject matter of Examples 29-34 includes, wherein the determination that the instrument is needed is based on machine learning.

In Example 36, the subject matter of Examples 29-35 includes, wherein the determination that the instrument is needed is based on a previously stored surgeon preference.

In Example 37, the subject matter of Examples 29-36 includes, wherein the determination that the instrument is needed is based on a probability using a selected workflow and a timer.

In Example 38, the subject matter of Examples 29-37 includes, wherein the determination that the instrument is needed includes receiving a request for the instrument, including at least one of a spoken command, a touch on a touchscreen, an interaction with an augmented reality user interface, or a gesture.

In Example 39, the subject matter of Examples 29-38 includes, wherein to provide access to the instrument, the processor is further configured to display an indication of the instrument using an augmented reality display device.

In Example 40, the subject matter of Examples 29-39 includes, wherein to provide access to the instrument, the processor is further configured to cause an enclosure of the sterilization unit to open, exposing the sterile environment including the instrument.

In Example 41, the subject matter of Examples 29-40 includes, wherein to provide access to the instrument, the processor is further configured to cause the surgical robotic arm to retrieve the instrument.

In Example 42, the subject matter of Examples 29-41 includes, wherein to provide access to the instrument, the processor is further configured to cause the instrument to be output from the sterilization unit via a mechanical conveyance.

In Example 43, the subject matter of Examples 29-42 includes, wherein to provide access to the instrument, the processor is further configured to provide a set of sterile instruments, including the instrument, for a procedure.

Example 44 is a system configured to perform operations of any of any of the methods of Examples 29-43.

Example 45 is at least one machine-readable medium including instructions for operation of a computing system, which when executed by a machine, cause the machine to perform operations of any of the methods of Examples 29-43.

Example 46 is an apparatus comprising means for performing any of the methods of Examples 29-43.

Example 47 is a method of using a surgical robotic system comprising: determining, using a processor, that an instrument, stored in a sterilization unit enclosing a sterile environment is needed in an upcoming portion of a surgical procedure; and providing access to the instrument from the sterilization unit that is mounted under or forms a base of a surgical robotic arm of the surgical robotic system.

In Example 48, the subject matter of Example 47 includes, wherein determining that the instrument is needed includes using a previously stored surgeon preference.

In Example 49, the subject matter of Examples 47-48 includes, wherein determining that the instrument is needed includes using a selected workflow and a timer implemented by the processor.

In Example 50, the subject matter of Examples 47-49 includes, wherein determining that the instrument is needed includes receiving a request for the instrument, including at least one of a spoken command, a touch on a touchscreen, an interaction with an augmented reality user interface, or a gesture.

In Example 51, the subject matter of Examples 47-50 includes, wherein providing access to the instrument includes displaying an indication of the instrument using an augmented reality display device.

In Example 52, the subject matter of Examples 47-51 includes, wherein providing access to the instrument includes causing the instrument to be output from the sterilization unit via a mechanical conveyance.

In Example 53, the subject matter of Examples 29-52 includes, wherein the instrument is adapted to connect to an end effector of the surgical robotic system (e.g., where the end effector is affixed to a distal end of the surgical robotic arm).

In Example 54, the subject matter of Examples 29-52 includes, wherein the surgical robotic system stores, or is connected to a database that stores, a schedule of upcoming cases, events, procedures, etc.

In Example 55, the subject matter of Example 54 includes, wherein the surgical robotic system performs a sterilization of the instrument during scheduled downtown, before an upcoming case, event, or procedure, or during off hours or unscheduled time.

Example 56 is at least one machine-readable medium including instructions that, when executed by processing circuitry, cause the processing circuitry to perform operations to implement of any of Examples 1-55.

Example 57 is an apparatus comprising means to implement of any of Examples 1-55.

Example 58 is a system to implement of any of Examples 1-55.

Example 59 is a method to implement of any of Examples 1-55.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A surgical robotic system comprising:
a surgical robotic arm;
a sterilization unit enclosing a sterile environment and storing an instrument, wherein the sterilization unit is mounted under or forms a base of the surgical robotic arm;
a processor configured to:
determine that the instrument is needed in an upcoming portion of a surgical procedure; and
provide access to the instrument.

2. The surgical robotic system of claim 1, wherein the sterilization unit is the base of the surgical robotic arm.

3. The surgical robotic system of claim 1, wherein the sterilization unit is a portable sterilization unit, and wherein the surgical robotic arm is configured to be mounted on the portable sterilization unit.

4. The surgical robotic system of claim 1, wherein the sterilization unit is a sterile storage unit without sterilization capabilities.

5. The surgical robotic system of claim 1, wherein the sterilization unit is configured to actively sterilize the instrument.

6. The surgical robotic system of claim 1, wherein the sterilization unit is configured to store a plurality of instruments including the instrument.

7. The surgical robotic system of claim 1, wherein the determination that the instrument is needed is based on a previously stored surgeon preference.

8. The surgical robotic system of claim 1, wherein the determination that the instrument is needed is based on a probability using a selected workflow and a timer implemented by the processor.

9. The surgical robotic system of claim 1, wherein the determination that the instrument is needed includes receiving a request for the instrument, including at least one of a spoken command, a touch on a touchscreen, an interaction with an augmented reality user interface, or a gesture.

10. The surgical robotic system of claim 1, wherein to provide access to the instrument, the processor is further configured to display an indication of the instrument using an augmented reality display device.

11. The surgical robotic system of claim 1, wherein to provide access to the instrument, the processor is further configured to cause an enclosure of the sterilization unit to open, exposing the sterile environment including the instrument.

12. The surgical robotic system of claim 1, wherein to provide access to the instrument, the processor is further configured to cause the surgical robotic arm to retrieve the instrument.

13. The surgical robotic system of claim 1, wherein to provide access to the instrument, the processor is further configured to cause the instrument to be output from the sterilization unit via a mechanical conveyance.

14. The surgical robotic system of claim 1, wherein to provide access to the instrument, the processor is further configured to provide a set of sterile instruments, including the instrument, for a procedure.

* * * * *